United States Patent [19]

Calanchi et al.

[11] Patent Number: 5,047,248
[45] Date of Patent: Sep. 10, 1991

[54] FORMULATION FOR PREPARING SUSTAINED RELEASE DRUGS FOR ORAL ADMINISTRATION

[75] Inventors: Massimo Calanchi; Leonardo Gentilini; Luigi Mapelli; Marco Meroni, all of Milan, Italy

[73] Assignee: Eurand Italia S.p.A., Milan, Italy

[21] Appl. No.: 308,120

[22] Filed: Feb. 8, 1989

Related U.S. Application Data

[63] Continuation of Ser. No. 114,658, filed as PCT EP 87/00124 on Mar. 3, 1987, published as WO 87/05212 on Sep. 11, 1987, abandoned.

[30] Foreign Application Priority Data

Mar. 7, 1986 [IT] Italy ............................ 19675 A/86

[51] Int. Cl.$^5$ ............................ A61K 9/22; A61K 9/52
[52] U.S. Cl. ............................ 424/485; 424/457; 424/465; 424/468
[58] Field of Search ............ 424/485, 500, 468, 457, 424/493, 455, 465

[56] References Cited

U.S. PATENT DOCUMENTS

| | | | |
|---|---|---|---|
| 3,065,143 | 11/1962 | Christenson et al. | 424/468 |
| 4,163,777 | 8/1979 | Mitra | 424/468 |
| 4,248,858 | 2/1981 | Guley et al. | 424/479 X |
| 4,259,341 | 3/1981 | Lowey | 514/369 |
| 4,332,789 | 6/1982 | Mlodozeniec | 424/443 X |
| 4,344,857 | 8/1982 | Shasha et al. | 424/485 X |
| 4,369,172 | 1/1983 | Schor et al. | 424/468 |
| 4,375,468 | 3/1983 | Dunn | 514/165 |
| 4,556,678 | 12/1985 | Hsiao | 424/465 X |
| 4,601,895 | 7/1986 | Streuff | 424/479 |
| 4,610,870 | 9/1986 | Jain et al. | 424/465 |
| 4,690,822 | 9/1987 | Uemura et al. | 424/455 |
| 4,695,467 | 9/1987 | Uemura | 424/502 |
| 4,704,285 | 11/1987 | Alderman | 424/465 X |
| 4,762,702 | 8/1988 | Gergely et al. | 424/500 X |

FOREIGN PATENT DOCUMENTS

| | | |
|---|---|---|
| 901111 | 3/1985 | Belgium. |
| 146863 | 12/1984 | European Pat. Off.. |
| 180364 | 10/1985 | European Pat. Off.. |
| 2143059 | 6/1972 | France. |
| 60-174728 | 9/1985 | Japan ............... 424/485 |
| 2055577 | 7/1980 | United Kingdom. |

*Primary Examiner*—Thurman K. Page
*Assistant Examiner*—Donald R. McPhail
*Attorney, Agent, or Firm*—Gordon W. Hueschen

[57] ABSTRACT

Pharmaceutical formulations are disclosed, adapted for preparing solid oral dosage forms (tablets, capsules, lozenges, etc.) having a regular and sustained release after administration. Said formulations comprise one or more active substances and a retarding base or matrix consisting of a polysaccharide of natural origin, alone or mixed with one or more natural or synthetic polymers which may be used to modify the release pattern so as to obtain a therapeutically effective formulation.

9 Claims, No Drawings

FORMULATION FOR PREPARING SUSTAINED RELEASE DRUGS FOR ORAL ADMINISTRATION

This is a continuation of application Ser. No. 114,658, filed as PCT EP 87/00124 on Mar. 3, 1987, published as WO 87/05212 on Sep. 11, 1987, now abandoned.

TEXT OF THE DESCRIPTION

The present invention relates to pharmaceutical formulations adapted to prepare solid oral dosage forms, such as capsules, tablets, lozenges and the like, having a regular and sustained release after administration.

The advantages of the sustained release or retard drugs are well known since a long time, because delaying the dissolution of the active substance, the absorption time in the gastrointestinal tract is extended, thus prolonging the therapeutic effect, at the same time avoiding or at least reducing the side effects.

For this purpose a retard formulation has to meet some criteria, namely causing a uniform and constant dissolution and being effective for an extended period of time. It is also important that such a formulation be simple to be made, the manufacturing process be reproducible and may be used for a high number of different substances.

There are several known methods for preparing retard products in the form of solid oral dosage such as tablets or capsules. Among these methods, delaying hydrophilic matrices are often used because the manufacture of finished form is simple and reproducible, it is possible to obtain a gradual and continuous release, they can be applied to many drugs and are economically advantageous.

Hydrophilic matrix is defined a homogeneous mixture of substances, substantially comprising polymers which are slowly dissolved in water and then receiving a well defined form by compression or encapsulation. When the tablet is contacted with water or aqueous based dissolution media as the gastro-intestinal juices, the hydrophilic polymers give rise to the formation of a gelatinous surface layer, through which water slowly penetrates inside, hydrating and swelling the polymer; then the polymer in the gel form, gradually goes in solution, first the outermost layer and thereafter the inner layers until it is totally dissolved and disappears.

In this way the active substance is totally and slowly released by two contemporaneous mechanisms, namely diffusion through the gelatinous layer and gel erosion.

While the first of these release mechanisms prevails in case of drugs very soluble in the dissolution medium, the second prevails in case of poorly soluble drugs.

The polymers suitable for the preparation of hydrophilic retard matrices are relatively few, but there are already patents and publications on this subject matter. U.S. Pat. No. 4,259,341 to Lowey, U.S. Pat. No. 3,870,790 to Lowey et al, U.S. Pat. No. 4,226,849 to Schor and U.S. Pat. No. 4,357,469 to Schor relate to the preparation of tablets with a hydrophilic matrix comprising hydroxypropylmethylcellulose, alone or mixed with other cellulose derivatives, having undergone particular treatment such as high drying, humidification, hydrolysis, oxidation.

Also U.S. Pat. Nos. 4,369,172 and 4,389,393 to Schor et al relate to the use of one or more types and well defined quantities of hydroxypropylmethylcellulose alone or mixed with methylcellulose and/or sodium carboxymethylcellulose.

U.S. Pat. Nos. 4,167,448 and 4,126,672 to Sheth et al relate to the use of hydroxypropylmethylcellulose for preparing tablets and more particularly capsules with hydrophilic matrix having such a composition that they remain floating in the gastric juices.

The article titled "A review of cellulose ethers in hydrophilic matrices for oral controlled release dosage forms by D. A. Alderman, published on Int. Journal Pharm. Techn. & Prod. Mfr. 5(3) 1-9, 1984, widely deals with the use of hydroxypropylmethylcellulose for preparing retard hydrophilic matrices and studies the influence on the drug release, of several parameters characteristic of hydroxypropylmethylcellulose such as molecular weight, substitution degree, grain size distribution, velocity of hydration.

The present invention relates to the use of a hydrophilic polymer of natural origin, namely xanthan gum as main constituents of formulations adapted to prepare hydrophilic retard matrices for the administration of drugs in the form of tablets, lozenges, capsules and so on. The main feature of this invention consists indeed in using xanthan gum to obtain retard matrices, this object having been attained up to now only using hydroxypropylmethylcellulose as single or main hydrophilic polymer. In the relevant literature moreover this xanthan gum is generally used in water solution as thickeners to stabilize emulsions, suspensions, creams, latices and the like, and their use as basic excipients for preparing solid matrices is never cited.

According to the present invention it was indeed found that the use of xanthan gum allows to obtain matrices giving a sustained and gradual drug release; moreover by varying the quantity of the xanthan gum in the formulation according to the solubility and dosage of the drug, it is possible to change the pattern of in vitro drug release. As a matter of fact xanthan gum, which is hydrophilic polymer of high molecular weight, when it comes in contact with water or gastrointestinal juices, give rapid rise to the formulation of a gelatinous surface layer controlling the further diffusion of water or gastrointestinal juices to the interior and consequently the drug release.

Water or juices penetrate inside the matrix in subsequent layers gradually transforming the polymer into a gelatinous mass and then dissolving it while active substance is at the same time released.

Another advantage of xanthan gum is that it allows to extend release of a great number of drugs, irrespective of their dosage and solubility, by employing economical and reproducible manufacturing processes.

Still another advantage is given by the possibility of preparing formulations giving rise to retard matrices releasing the drug even in very long times that may even reach 24 hours so as to allow only one single administration per day.

Xanthan gum is a high molecular natural carbohydrate and more particularly an exocellular biopolysaccharide produced by a fermentation process of the microorganism Xanthomonas campestris. Structure, molecular weight and properties of dissolution of this natural polymer are constant and reproducible under strictly controlled operative conditions. Xanthan gum, known also under the trade names of Keltrol ® and Kelzan ®, is used in many fields, such as the food, drug and cosmetic field. In these cases the thickening and stabilizing property of emulsions or suspensions given by xanthan gum in solution is used.

With the present invention it was found that it is possible to utilize the properties of xanthan gum even for solid formulations of drugs, using it for preparing hydrophilic matrices in which xanthan gum has the effect of delaying the drug dissolution.

Matrix may comprise either xanthan gum alone or a mixture of xanthan gum with other natural or synthetic polymers, having the effect of varying the drug release curve so as to obtain those more adapted to reach the maximum in vivo bioavailability and efficiency thereof.

Therefore it is possible to mix to xanthan gum the following:

1) polymers hydrating and dissolving in water such as methylcellulose, hydroxyethylcellulose, gum arabic, polyvinylpyrrolidone, gelatine;
2) polymers having a pH dependent solubility such as shellac, cellulose acetophtalate, xydroxypropylmethylcellulose phtalate, polyvinylacetophtalate, polyacrylates;
3) polymers hydrating and dissolving slowly in water, such as xydroxypropylmethylcellulose, modified starch and rubber of natural origin.

Matrix is therefore comprising xanthan gum, in a percentage varying between 31 and 100% and preferably between 50 and 100%, alone or mixed with one or more polymers of one or more of the three above mentioned groups, in a quantity between 0 and 69% and preferably between 0 and 50%.

The retarding matrix is mixed in a suitable apparatus with the drug or even more drugs, which are intended to be administrated in a sustained release form. Among the possible drugs, the following are cited as illustrative non limiting examples only:

adrenergic amines (ethylephrine, phenylephrine, phenylpropanolamine, d-pseudoephedrine), antispasmodics (scopolamine and other belladonna alkaloids, papaverine and its derivatives), antihistaminics (bronchopheniramine, chloropheniramine, diphenylpyraline, dimenhydrinate), anorexics (norpseudoephedrine, phenermine, diethylpropione, phenfluramine), antiasthmatics (theophylline, sulbutamol, terbutaline), antianginics (isosorbide-5-mononitrate, isosorbide dinitrate, pentaerythritol tetranitrate, nitroglycerin, nifedipine, dilthiazem), antiflammatories and antipyretics (indomethacine, ibuprofen, ketoprofen, acetylsalicylic acid, paracetamol, phenacetine), hypotensives (nifedipine, hydrolazine, prazosine, verapamil), antidepressants (anitryptiline, lithium salt), antitussives (dextromethorphane, noscapine, codeine), gastroenterics (cimetidine, ranitidine, methoclopramide), antiarrhythmics (procainamide, lidocaine, flecainide, propophenone), analgesics (morphine), vitamins (ascorbic acid) and their salts used in the pharmaceutical field.

In addition to polymers and drugs, in the formulation there may be also inert excipients commonly used by men skilled in the art to improve the characteristics of said formulation.

Thus for instance, lubricants, dyestuffs, sweeteners, flavouring agents, inert excipients and so forth may be added in the preparation of tablets in order to improve flowance of powders, appearance, taste, dosage precision and the like.

The quantity of matrix used to delay drug release may therefore be varied in a broad interval, depending whether the formulation comprises only drug and matrix or other excipients are present in a more or less high amount according to the high or low level of solubility and/or the high or low dosage of the active substance.

Therefore said matrix may vary between 10 and 80% by weight of the formulation and preferably between 20 and 60% by weight.

The following examples are intended to better clarify the invention and it is to be understood that they are not limiting the scope of the invention, as many variations may be readily apparent to a man skilled in the art.

EXAMPLE 1-3

Sustained release tablets of theophylline (dosage 350 mg) were prepared, containing the percentages of delaying substances set forth in the following table:

| Example No | Xanthan gum % | Hydroxypropylcelluose % |
|---|---|---|
| 1 | 27.2 | 9.0 |
| 2 | 19.8 | 9.9 |
| 3 | 10.1 | 10.1 |

Tablets of 350 mg each were prepared with the following excipients:

| | Example 1 | | Example 2 | | Example 3 | |
|---|---|---|---|---|---|---|
| Ingredients | g | mg/tablet | g | mg/tablet | g | mg/tablet |
| (1) Theophylline | 105.0 | 350.0 | 105.0 | 350.0 | 105.0 | 350.0 |
| (2) Xanthan gum | 45.0 | 150.0 | 30.0 | 100.0 | 15.0 | 50.0 |
| (3) Hydroxypropylcellulose | 15.0 | 50.0 | 15.0 | 50.0 | 15.0 | 50.0 |
| (4) Flame silica | 0.6 | 2.0 | 0.6 | 2.0 | 0.6 | 2.0 |
| (5) Magnesium stearate | 0.8 | 3.0 | 0.9 | 3.0 | 0.9 | 0.3 |

The ingredients 1, 2 and 3 were mixed for 15 minutes. Then ingredient 4 was added and after further 15 minutes of mixing, also the ingredient 5 was added. The mixture was agitated for 10 minutes and then subjected to compression in a tabletting machine with punches of $15 \times 6$ mm (r=5.0 mm) to make about 250 candle shaped tablets with double fracture line.

Samples were obtained having the following characteristics:

| Sample | Average weight mg/tablet | Thickness mm | Harness Kg | Friability 10 × 4 % |
|---|---|---|---|---|
| 1 | 555 | 5.88 | 13.1 | 0.26 |
| 2 | 505 | 5.33 | 13.4 | 0.20 |
| 3 | 455 | 4.85 | 13.7 | 0.22 |

Hardness of the tablets was determined with the apparatus Erweka TBH 28 and friability with the apparatus Roche Friabilator at 25 rpm checking the loss of weight of 10 tablets after 4 minutes of rotation.

In vitro release of the tablets was determined with the rotary blade method described in USP, XXI ed., page 1244, employing according to the kind of analysis, the proper vessels containing 500 ml of artificial gastric juice (pH 1.2) or 500 ml of artifical intestinal juice (pH 6.8) preheated at 37° C. The vessels were closed and agitator was regulated at a speed of 150 rpm. In each vessel a tablet corresponding to 350 mg of active substance was added.

At predetermined intervals of 1, 2, 4, 8, 12 and 14 hours a sample of 5 ml was taken and the vessel refilled with the same amount of juice or fluid. The sample was suitably diluted and analyzed at the spectrophotometer at a wavelength of 270 nm in 100N HCl against standard reference.

The results of the analysis, given in the following table, show that the release of theophylline occurs in 12 or more hours according to the matrix composition.

| Sample | Buffer pH | Cumulative release % | | | | | |
|---|---|---|---|---|---|---|---|
| | | 1 h | 2 h | 4 h | 8 h | 12 h | 14 h |
| 1 | 1.2 | 10.5 | 17.0 | 27.2 | 40.7 | 51.9 | 58.2 |
| | 6.8 | 7.8 | 12.8 | 22.4 | 47.8 | | |
| 2 | 1.2 | 11.8 | 18.8 | 30.3 | 49.8 | 61.4 | 66.3 |
| | 6.8 | 9.1 | 15.7 | 24.9 | 48.1 | | |
| 3 | 1.2 | 17.2 | 25.6 | 39.7 | 71.4 | 93.8 | 100.0 |
| | 6.8 | 15.6 | 25.6 | 42.5 | 70.6 | | |

EXAMPLES 4-5

Theophylline tablets (dosage 350 mg) were prepared, in which the delaying substances are present in the amount given below:

| Example No | Xanthan gum % | Hydroxypropyl-methylcellulose % | Hydroxypropyl-cellulose % |
|---|---|---|---|
| 4 | 11.0 | 5.5 | 5.5 |
| 5 | 10.9 | 10.9 | — |

Tablets of 350 mg each were prepared with the following excipients:

| | Example 4 | | Example 5 | |
|---|---|---|---|---|
| Excipients | g | mg/tablet | g | mg/tablet |
| Theophylline | 105.0 | 350.0 | 105.0 | 350.0 |
| (1) Xanthan gum | 15.0 | 50.0 | 15.0 | 50.0 |
| (2) Hydroxypropyl-cellulose | 7.5 | 25.0 | 15.0 | 50.0 |
| (3) Hydroxypropyl methylcellulose | 7.5 | 25.0 | — | — |
| (4) Flame silica | 0.6 | 2.0 | 0.6 | 2.0 |
| (5) Magnesium stearate | 1.5 | 3.0 | 1.5 | 5.0 |

Mixing was effected in the manner described in Examples 1-3. The mixture was subjected to compression in a tabletting machine with punches 15×6 mm (r=5 mm) to make about 250 candle-shaped tablets with double fracture line. The samples had the following characteristics:

| Sample No | Average Weight mg/tablet | Thickness mm | Hardness Kg | Friability % |
|---|---|---|---|---|
| 4 | 457 | 4.87 | 13.4 | 0.1 |
| 5 | 457 | 4.85 | 13.7 | 0.1 |

Hardness and friability of the tablets were measured with the apparatus described in Examples 1-3.

In order to check the in vitro release, the same method used for Example 1-3 was employed and the results given in the following table were found, from which one can see the delayed release of the drug due to the xanthan gum based matrix.

| Sample No | Buffer pH | Cumulative release % | | | | | |
|---|---|---|---|---|---|---|---|
| | | 1 h | 2 h | 4 h | 8 h | 12 h | 14 h |
| 4 | 1.2 | 17.8 | 29.0 | 47.4 | 80.2 | 95.9 | |
| | 6.8 | 12.6 | 23.2 | 38.7 | 58.8 | 79.7 | |
| 5 | 1.2 | 15.3 | 25.1 | 40.5 | 65.5 | 88.7 | 100 |
| | 6.8 | 12.3 | 21.0 | 34.2 | 55.1 | 81.4 | 100 |

EXAMPLE 6

Theophylline tablets (dosage 350 mg) were prepared, containing as delaying substance 22% xanthan gum. The tablets had the following composition:

| Ingredients | Example 6 | |
|---|---|---|
| | g | mg/tablet |
| Theophylline | 105.0 | 350.0 |
| Xanthan gum | 30.0 | 100.0 |
| Flame silica | 0.6 | 2.0 |
| Magnesium stearate | 0.9 | 3.0 |

Mixing was effected as in Examples 1-3. Mixture was subjected to compression in a tabletting machine with punches 15×6 mm (r=5 mm) to make about 250 candle shaped tablets with double fracture line having the following characteristics:

| Sample No | Average weight mg/tablet | Thickness mm | Hardness Kg | Friability % |
|---|---|---|---|---|
| 6 | 455 | 4.85 | 13.76 | 0.2 | and the following in vitro release:

| Sample No | Buffer pH | Cumulative release % | | | | | |
|---|---|---|---|---|---|---|---|
| | | 1 h | 2 h | 4 h | 8 h | 12 h | 14 h |
| 6 | 1.2 | 12.5 | 20.2 | 31.2 | 45.9 | 58.1 | 63.8 |
| | 6.8 | 7.6 | 13.8 | 25.4 | 45.9 | 88.9 | 100.0 |

EXAMPLE 7

Tablets of 50 mg of amitryptilline retard were prepared containing 16.6% of xanthan gum and 16.6% of hydroxypropylcellulose, as costituents of the delaying matrix.

The tablets of 50 mg were prepared with the following excipients:

| Ingredients | Example 7 | |
|---|---|---|
| | g | mg/tablet |
| Amitryptiline | 25 | 50.0 |
| Xanthan gum | 10 | 20.0 |
| Hydroxypropylcellulose | 10 | 20.0 |
| Lactose | 13.75 | 27.5 |
| Flame Silica | 0.25 | 0.5 |
| Magnesium stearate | 1.00 | 2.0 |

Mixing was effected as in Examples 1-3. The mixture was subjected to compression in a tabletting machine with punches 4×9 mm to make about 350 flat candle tablets. The samples had the following characteristics:

| Sample No | Average weight mg/tablet | Hardness Kg | Frability % |
|---|---|---|---|
| 7 | 120 | 7.06 | 0.1 |

Hardness and friability of the tablets were measured with the apparatus described in Examples 1-3.

In order to check the in vitro release the same method used in Examples 1-3 was employed and the following results were obtained:

| Sample No | Buffer pH | Cumulative release % | | | | |
|---|---|---|---|---|---|---|
| | | 1 h | 2 h | 4 h | 8 h | 12 h | 14 h |
| 7 | 12.2 | 33.3 | 48.8 | 72.8 | 100 | | |

EXAMPLES 8-9

Retard tablets of methoclopramide chlorohydrate were prepared with a dosage of 30 mg of methoclopramide, containing either 29.2% xanthan gum, 14.6% hydroxypropylcellulose and 14.6% hydroxypropylmethylcellulose (Ex. 8) or 31.9% xanthan gum and 31.9% hydroxypropylmethylcellulose (Ex. 9) as constituents of the delaying matrix. The tablets of 30 mg methoclopramide were prepared with the following excipients:

| Excipients | Example 8 | | Example 9 | |
|---|---|---|---|---|
| | g | mg/tablet | g | mg/tablet |
| Methoclopramide HCl | 16.8 | 33.7 | 16.8 | 33.7 |
| Xanthan Gum | 17.5 | 35.0 | 17.5 | 35.0 |
| Hydroxypropylcellulose | 8.7 | 17.5 | | |
| Hydroxypropylmethylcellulose | 8.7 | 17.5 | 17.5 | 35.0 |
| Spray Dry Lactose | 5.1 | 10.3 | | |
| Flame silica | 1.0 | 2.0 | 1.0 | 2.0 |
| Magnesium Slearate | 2.0 | 4.0 | 2.0 | 4.0 |

Mixing was effected in the same manner as in Examples 1-3. The mixture was subjected to compression in a tabletting machine with punches 4×9 mm to make about 500 flat candle tablets having the following characteristics:

| Sample No | Average weight mg/tablet | Hardness Kg | Friability % |
|---|---|---|---|
| 8 | 123 | 9.8 | 0.2 |
| 9 | 114 | 11.6 | 0.2 |

Hardness and friability of the tablets were measured with the apparatus described in Examples 1-3. In order to check the in vitro release the same method of Examples 1-3 was used with the only change that the agitator was set at a speed of 125 rpm instead of 150 rpm.

The methoclopramide tablets had the following in vitro release:

| Sample | Buffer pH | Cumulative release % | | | | | |
|---|---|---|---|---|---|---|---|
| | | 1 h | 2 h | 4 h | 8 h | 12 h | 16 h |
| 8 | 1.2 | 41.2 | 59.5 | 82.8 | 96.3 | 100.0 | |
| | 6.8 | 35.2 | 49.1 | 68.7 | 82.0 | 91.3 | 97.6 |
| 9 | 1.2 | 34.1 | 49.9 | 71.6 | 94.0 | 100.0 | |
| | 6.8 | 28.6 | 41.8 | 60.7 | 82.9 | 94.1 | 99.2 |

Retard tablets of methoclopramide chlorohydrate of 30 mg methoclopramide were prepared, containing 58.6% xanthan gum as a delaying substance. The 30 mg methoclopramide tablets were prepared with the following excipients:

| Ingredients | Example 10 | |
|---|---|---|
| | g | mg/tablet |
| Methoclopramide HCl | 16.8 | 33.7 |
| Xanthan gum | 35.1 | 70.3 |
| Spray Dry Lactose | 5.0 | 10.0 |
| Flame silica | 1.0 | 2.0 |
| Magnesium stearate | 2.0 | 4.0 |

Mixing was effected in the same manner as in Examples 1-3. The mixture was subjected to compression in a tabletting machine with punches 4×9 mm to make about 500 flat candle tablets having the following characteristics:

| Sample No | Average weight mg/tablet | Hardness Kg | Friability % |
|---|---|---|---|
| 10 | 126.4 | 7.7 | 0.2 |

Hardness and friability of the tablets were measured with the apparatus described in Examples 1-3. In order to check the in vitro release the same method used for Examples 8 and 9 was employed. The tablets had the following in vitro release:

| Sample No | Buffer pH | Cumulative release % | | | | | |
|---|---|---|---|---|---|---|---|
| | | 1 h | 2 h | 4 h | 8 h | 12 h | 16 h |
| 10 | 1.2 | 43.8 | 61.5 | 84.0 | 100 | | |
| | 6.8 | 27.8 | 41.8 | 61.6 | 85.4 | 93.5 | 98.6 |

EXAMPLES 11-13

Retard tablets of theophylline with a dosage of 350 mg were prepared, containing the percentages of delaying substances indicated in the following table:

| Example No | Instant Cleargel ® % | Hydroxypropylcellulose % |
|---|---|---|
| 11 | 26.9 | 9.0 |
| 12 | 19.7 | 9.0 |
| 13 | 10.9 | 10.9 |

The tablets of 350 mg were prepared with the following excipients:

| Ingredients | Example 11 | | Example 12 | | Example 13 | |
|---|---|---|---|---|---|---|
| | g | mg/tablet | g | mg/tablet | g | mg/tablet |
| Theophylline | 105 | 350 | 105 | 350 | 105 | 350 |
| Instant Cleargel | 45 | 150 | 30 | 100 | 15 | 50 |
| Hydroxypropylcellulose LF | 15 | 50 | 15 | 50 | — | — |
| Hydroxypropylcellulose HF | — | — | — | — | 15 | 50 |
| Flame silica | 0.6 | 2 | 0.6 | 2 | 0.6 | 2 |
| Magnesium stearate | 1.5 | 5 | 1.5 | 5 | 1.5 | 5 | was compressed in a tabletting machine with punches 15×6 mm (r=5 mm) to make about 250 candle shaped tablets with double fracture line. The samples had the following characteristics:

| Sample No | Average weight mg/tablet | Thickness mm | Hardness Kg | Friability % |
|---|---|---|---|---|
| 11 | 557 | 5.00 | 13.1 | 0.1 |
| 12 | 507 | 5.56 | 13.7 | 0.1 |
| 13 | 457 | 5.12 | 15.6 | 0.1 |

Hardness and friability of the tablets were measured with the apparatus described in Examples 1-3.

In order to check the in vitro release the same method used for Examples 1-3 was employed and the results are given in the following table, where one can see the delaying effect of drug release due to the maxtrix based on Instant Cleargel ®:

| Sample No | Buffer pH | Cumulative release % | | | | | |
|---|---|---|---|---|---|---|---|
| | | 1 h | 2 h | 4 h | 8 h | 12 h | 14 h |
| 11 | 1.2 | 20.2 | 38.1 | 60.3 | 81.2 | | |
| 12 | 1.2 | 28.3 | 45.1 | 68.5 | 88.1 | | |
| 13 | 1.2 | 28.1 | 35.4 | 48.7 | 71.9 | 87.0 | 93.5 |
| | 6.8 | 31.2 | 37.9 | 49.6 | 70.0 | 84.7 | 91.5 |

EXAMPLE 14

Theophylline tablets with a dosage of 350 mg were prepared, containing as delaying substance 22% of Instant Cleargel ®. The tablets had the following composition

| Ingredients | Example 14 | |
|---|---|---|
| | g | mg/tablet |
| Theophylline | 105 | 350 |
| Instant Cleargel | 30 | 100 |
| Flame silica | 0.6 | 2 |
| Magnesium Stearate | 1.5 | 5 |

Mixing was effected as in Examples 1-3. The mixture was subjected to compression in a tabletting machine with punches 15×6 mm (r=5 mm) to make about 250 candle-shaped tablets with double fracture line having the following characteristics:

| Sample No | Average weight mg/tablet | Thickness mm | Hardness Kg | Friability % |
|---|---|---|---|---|
| 14 | 457 | 5.00 | 14.1 | 0.1 | and the following in vitro release:

| Sample No | Buffer pH | Cumulative release % | | | |
|---|---|---|---|---|---|
| | | 1 h | 2 h | 4 h | 8 h |
| 14 | 1.2 | 28.1 | 35.4 | 48.7 | 71.9 |

EXAMPLE 15

Hard gelatin capsule (size 1, transparent neutral colour) of theophylline (dosage 100 mg) were prepared, containing as delaying substance 33.3% of xanthan gum with the following composition:

| Ingredients | Example 15 | |
|---|---|---|
| | g | mg/tablet |
| Theophylline | 30 | 100 |
| Xanthan gum | 60 | 200 |

The mixture was prepared as in the Examples 1-3.

The capsules were filled with a laboratory capsule filling machine of the Zuma type in order to make 300 capsules.

For controlling the in vitro release the same method used for Examples 1-3 was employed, with the only variant that the agitator was set at a speed of 75 rpm instead 150 rpm.

The theophylline release from the capsules is delayed by the Xanthan gum matrix as shown by the following values of in vitro release:

| Sample No | Buffer pH | Cumulative release % | | | |
|---|---|---|---|---|---|
| | | 1 h | 2 h | 4 h | 8 h |
| 15 | 1.2 | 21.2 | 36.3 | 60.1 | 83.0 |

It is therefore clear, from the foregoing description and the illustrative examples, that the desired objects are fully attained, while it is also to be understood that many variations, modifications, additions and/or substitutions of elements may be resorted to the formulations according to the present invention, without departing however from its spirit and objects and without falling outside its scope of protection, as it is defined in the appended claims.

We claim:

1. Formulation for preparing solid dosage forms having a regular and sustained release, characterized by consisting essentially of an effective amount of a pharmaceutically active substance and 10-80 weight percent of a matrix, being a homogeneous mixture of substances imparting a retard effect, said matrix consisting essentially of 31-100 weight percent of xanthan gum, said pharmaceutically active substance being intimately admixed into said matrix.

2. Formulation of claim 1 for preparing solid dosage forms having a regular and sustained release, characterized by consisting essentially of said active substance and 20-80 weight percent of a matrix, imparting a retard effect, said matrix consisting essentially of 31-100 weight percent of xanthan gum and 0-69 weight percent of one or more natural or synthetic polymers, which hydrate and dissolve slowly and/or quickly in water or in gastrointestinal juices or which have a dissolution velocity which is a function of the pH value of the medium.

3. Formulation according to claim 2, characterized in that the percentage by weight of matrix components is 50-100% of xanthan gum and 0-50% of one or more of said polymers.

4. Formulation according to claim 2, characterized in that the matrix comprises, in addition to xanthan gum, hydroxypropylcellulose or hydroxypropylmethylcellulose or mixtures thereof.

5. Formulation according to claim 1 formulated into a sustained release pharmaceutical solid dosage form.

6. Formulation according to claim 2 wherein, in addition to said active substance and constituents of the matrix, an inert excipient used for obtaining the desired dosage form, selected from and lubricants, dyestuffs, diluents, sweeteners, lavouring agents are present.

7. Formulation according to claim 2 characterized in that the matrix has such a composition as to prolong the drug release up to 24 hours so as to allow one single administration per day.

8. A formulation of claim 5 wherein the dosage form is an oral dosage form.

9. A formulation of claim 8, wherein the oral dosage form is a tablet, capsule, or lozenge.

* * * * *

UNITED STATES PATENT AND TRADEMARK OFFICE
CERTIFICATE OF CORRECTION

PATENT NO. : 5,047,248

DATED : Sep. 10, 1991

INVENTOR(S) : Massimo Calanchi, Leonardo Gentilini, Luigi Mapelli, Marco Meroni It is certified that error appears in the above-identified patent and that said Letters Patent is hereby corrected as shown below:

Title Page, Related U.S. Application Data, [63], second line;
   "Mar. 3," should read -- Mar. 2, --
Column 1, line 5; "Mar. 3," should read -- Mar. 2, --.
Column 2, line 8; "forms by" should read -- forms" by --.
Column 2, line 34; delete "the", second occurrence.
Column 4, line 15; "Hydroxypropylcelluose" should read
   -- Hydroxypropylcellulose --.
Column 4, line 46; "Harness" should read -- Hardness --.
Column 7, approximately line 34; "Slearate" should read --Stearate--.
Column 10, line 58; delete "and".
Column 10, line 59; sweeteners, lavouring" should read --
   -- sweeteners, and flavouring --.
Column 10, line 59; "agents are present" should read
   -- agents, is present --.

Signed and Sealed this

Sixteenth Day of March, 1993

*Attest:*

STEPHEN G. KUNIN

*Attesting Officer*    *Acting Commissioner of Patents and Trademarks*